United States Patent [19]

Majeed et al.

[11] Patent Number: 5,804,596
[45] Date of Patent: Sep. 8, 1998

[54] METHOD OF PREPARING A FORSKOHLIN COMPOSITION FROM FORSKOHLIN EXTRACT AND USE OF FORSKOHLIN FOR PROMOTING LEAN BODY MASS AND TREATING MOOD DISORDERS

[75] Inventors: Muhammed Majeed; Vladimir Badmaey, both of Piscataway, N.J.; R. Rajendran, Bangalora, India

[73] Assignee: Sabinsa Corporation, Piscataway, N.J.

[21] Appl. No.: 807,652

[22] Filed: Feb. 27, 1997

[51] Int. Cl.⁶ .................................................. A61K 31/35
[52] U.S. Cl. .............................................................. 514/455
[58] Field of Search ............................................. 514/455

[56] References Cited

PUBLICATIONS

Hoffman, et al., *Horm. metabol. Res.*, 19 (1987) pp. 358–360, "Stimulation and Inhibition of Lipolysis in Isolated Rat Adipocytes: Evidence for Age–Related Changes in Responses . . . ".

Allen, et al., *The Journal of Pharmacology and Experimental Therapeutics*, vol. 238, Not. 2, pp. 659–664, "Relationships between cyclic AMP Levels and Lipolysis in Fat Cells After . . . ".

Allen, et al., *The Journal of Pharmacology and Experimental Therapeutics*, vol. 244, No. 3, pp. 852–858, "Quantitative Differences in the Cyclic AMP–Lipolysis Relationships for . . . ".

Wachtel, et al, *Psychopharmacology* (1986) 90 pp. 430–435, "Effects of forskolin and cyclic nucleotides in animal models predictive of antidepressant activity: interactions with rolipram".

*Primary Examiner*—Jerome D. Goldberg
*Attorney, Agent, or Firm*—Nikaido Marmelstein Murray & Oram LLP

[57] ABSTRACT

A method of promoting lean body mass in an individual is disclosed, comprising administering to the individual a lean body mass promoting effective amount of forskohlin. A method of treating a mood disorder is also disclosed, comprising administering to a patient in need thereof a mood disorder treating effective amount of forskohlin. Compositions suitable for promoting lean body mass and/or treating a mood disorder are also disclosed, the composition comprising about 1 to about 40% forskohlin in combination with at least one physiologically acceptable carrier or excipient. A method of preparing a forskohlin composition from a forskohlin extract of Coleus Forskoli plant is further disclosed, as well as a forskohlin composition prepared by the method.

8 Claims, No Drawings ary aids are designed to decrease the amount of body fat
METHOD OF PREPARING A FORSKOHLIN COMPOSITION FROM FORSKOHLIN EXTRACT AND USE OF FORSKOHLIN FOR PROMOTING LEAN BODY MASS AND TREATING MOOD DISORDERS

BACKGROUND OF THE INVENTION

Most weight loss pharmaceutical compositions and nutraceutical aids are designed to decrease the amount of body fat in an individual by decreasing the individual's appetite for food, decreasing the amount of food absorption in the individual, slowing down the rate of fatty acid synthesis within the body, or increasing the rate of catabolism of fatty acids. The following are some examples of weight loss products and their mechanisms. Dexfenfluramine increases the brain levels of serotonin, a neurotransmitter and neurohormone that quells the appetite. Sibutramine also increases the levels of serotonin, as well as noradrenaline, and works to quell the appetite. Neuropeptide Y inhibitors curb the appetite, as well as stimulating the body to burn more sugars and less fat. Bromeriptine mimics the neurotransmitter dopamine, and may reduce blood sugar and fat production by the liver. Leptin, a hormone generated by adipocytes, affects the hypothalamus. Cholecystokinin, a hormone and neurotransmitter, acts to reduce appetite. Butabindide blocks an enzyme that inactivates cholecystokinin. Orlistat interferes with pancreatic lipase, which results in poor absorption of dietary fat. Insulinotropin is a glucagon-like hormone which prevents obesity by slowing down the emptying of the stomach. Bta-243 stimulates beta-adrenergic receptors on adipocytes, with a resulting increase in the burning of fatty acids. Troglitazone is a synthetic hormone which signals muscle cells to utilize fat for energy, rather than sugars. Cytokine regulators change the activity of hormone-like cytokines and alter the communication among cells, resulting in weight loss. Hydroxycitric acid acts as an inhibitor of enzyme citrate lyase, which subsequently slows down the synthesis of fatty acids and increases the rate at which fatty acids are burned.

The average amount of body fat in the American male is 22 to 25%, and in the American female, the average amount of fat is 33 to 35%. These values are far above optimal values, which are 15 to 19% for 20–29 year old males and 19 to 23% for 20–29 year old females. Corresponding values for 40–49 year olds are 17 to 21% and 21 to 25%, respectively; and for 60 year olds, the corresponding values are 19 to 23% and 23 to 27%, respectively. In highly overweight individuals, fat tissue can constitute up to 70% of body weight.

The remaining percentage of body composition corresponds to the lean body mass. Lean body mass is composed of muscle, vital organs, bone, connective and other non-fatty tissues in the body, and most of the body water. The body's metabolic rate is in direct proportion to the amount of lean body mass. Therefore, considering the lean body mass is important for any weight loss strategy.

The aforementioned weight control means do not take into account the importance of maintaining or increasing the lean body mass in the process of weight loss. In fact, regimens to decrease body fat often contribute to the catabolic wasting of lean body mass. Increased lean body mass regulates body metabolism and helps in losing weight, as well as maintaining the accomplished weight reduction. On the other hand, diminished lean body mass slows down body metabolism and results in difficulties in maintaining an appropriate, healthy body weight. Thus, an ideal weight management approach should be to reduce body weight to acceptable levels by restoring the optimal proportions of fat to lean body mass. By maintaining or increasing the lean body mass while simultaneously reducing body fat, the weight loss regimen would serve the general purpose of improving the overall health of the individual.

Maintaining or increasing the lean body mass (for example, skeletal muscles) is one of the important considerations for any weight loss strategy because lean body mass determines the rate of metabolism and the body's thermogenic response to food, and food induced thermogenesis and the metabolic rate, in turn, control body weight by an increase in the catabolism of body fat. This is so because thermogenesis is preferentially fueled by fatty acids derived from stores of body fat and from food. In addition, a high rate of thermogenesis contributes to more food being absorbed and to the preferential build-up of lean body mass, rather than adipose tissue.

It is well known in the literature that forskohlin is related to lipolysis in isolated fat cells in vitro. See, for example, *Horm. metabol. Res.* 19 (1987), pp. 358–360; *J. Pharmacology and Experim. Therapeutics* 238 (1986), pp. 659–664; *J. Pharmacology and Experim. Therapeutics* 244 (1988), pp. 852–858. The biological mechanism for this action seems to be that forskohlin increases the levels of cyclic AMP (cAMP) or exerts action similar to cAMP. The following other biological effects of forskohlin have been described as a result of the cAMP or cAMP-like mechanisms: inhibition of platelet aggregation, increased chronotropic and inotropic effect on the heart, hypotensive action, bronchodilating action, potentiation of insulin secretion, increased synthesis of body steroids, increased release of adrenocorticotropic hormone (ACTH) and decreased intraocular pressure. However, the use of forskohlin for the promotion of lean body mass has not been reported.

Forskohlin has also been shown to be effective for reversing hypothermia or hypokinesia in mice depleted of presynaptic endogenous monoamines by pretreatment with reserpine, α-methyl-p-tyrosine and p-chlorophenylalanine, when the forskohlin is co-administered with cyclic nucleotide analogs dibutyryl cAMP (dBcAMP), 8-bromo cAMP (8-BrcAMP) and dibutyryl cGMP (dBcGMP). See *Psychopharmacology* 90 (1986), pp. 430–435. The authors of this study noted that antagonism of reserpine-induced hypothermia and hypokinesia are regarded as classic tests for predictions of possible clinical antidepressant activity. However, no reports exist showing that forskohlin can be effective in treating mood disorders such as depression and anxiety in humans. Such mood disorders are damaging in their own respects to the health of the individual, but also can, in some cases, lead to overeating and secondary obesity which further damages the health of the individual. Thus, a health regimen should also require that the individual be emotionally stable and highly motivated.

The present inventors know of no published or patented method of preparing a forskohlin composition from a forskohlin extract of the *Coleus Forskohli* plant. Such a method would be useful for providing a more pure form of forskohlin than that which is presently available on the market, and for providing a standardized amount of active forskohlin, which can thereafter be further processed by other manufacturers, or combined with nutritional supplements by end users.

SUMMARY OF THE INVENTION

The present invention relates to a method of promoting lean body mass in an individual, comprising administering to the individual a lean body mass promoting effective amount of forskohlin.

Further subject matter of the invention is a method of treating a mood disorder in a patient in need of such treatment, comprising administering to the patient a mood disorder treating effective amount of forskohlin. The mood disorder can be, for example, depression or anxiety.

The present invention also relates to a composition comprising an amount of forskohlin in combination with a physiologically acceptable carrier or excipient.

Yet another subject matter of the invention is a method of preparing a forskohlin composition from a forskohlin extract of *Coleus Forskohli* plant, comprising:

(a) providing a forskohlin extract of *Coleus Forskohli* plant;

(b) dissolving the forskohlin extract in a first solvent;

(c) thereafter separating an amount of forskohlin from an amount of impurities in a step comprising combining the product produced in step (b) with a second solvent, wherein the amount of forskohlin is insoluble in the second solvent and the amount of impurities are soluble in the second solvent; and (d) preparing a forskohlin composition by combining the amount of forskohlin obtained in step (c) with at least one physiologically acceptable carrier or excipient to produce a forskohlin composition having a predetermined forskohlin content.

The present invention also includes compositions prepared from the above method, as well as methods of promoting lean body mass and treating mood disorders using the compositions thus prepared.

DESCRIPTION OF THE PREFERRED EMBODIMENTS

The present invention shifts the proportion between lean body mass and adipose tissue in favor of lean body mass in order to restore the ideal physiological proportions between lean and fat body mass, thus improving the overall health status of the individual. The positive health effect of the invention can be measured by decreases in the waist hip ratio (WHR) and the body mass index (BMI), both good predictors of morbidity and mortality.

Without being bound by any theory, the present inventors believe that the invention increases the lean body mass by stimulating the enzyme adenylate cyclase (AC), with a resulting increase in the levels of cAMP. The increase levels of cAMP in the tissues correspond well to enhancing the thermogenic response to food. An increase in the thermogenic response to food, in turn, improves absorption of nutrients and their preferential incorporation into lean body mass. Thus, the formation of lean body mass is promoted.

Again without being bound by any theory, the present inventors believe that the mechanism of the invention specifically works as follows:

forskohlin stimulates noradrenaline released from the sympathetic nerves to interact with beta-adrenergic receptors;

this results in an increase in AC enzyme, with a subsequent rise in cAMP levels;

cAMP stimulates the activity of a protein kinase which phosphorylates a hormone-sensitive lipase to produce the active form of this enzyme;

the lipase stimulates the release of fatty acids from body adipose depots;

the released fatty acids stimulate the uncoupling process in the mitochondria, resulting in thermogenesis and provision of fuel to increase thermogenesis;

there is an increase in T4 5' deiodinase, which activates the thermogenic thyroid hormone T3;

there is an increase in the beta-adrenergic dependent metabolic functions, which leads to an increase in the lean body mass, i.e., activation of phosphorylase in skeletal muscles, insulin secretion, and the synthesis and secretion of anabolic steroid hormones.

Regarding the control of mood disorders, without being bound by any theory, the present inventors believe that the biological mechanism by which forskohlin treats these disorders is as follows:

forskohlin restores the level of monoamines for presynaptic availability, which has known anti-depressant action;

there is an increase in cAMP in the postsynaptic effector cells in the brain, which is a "second messenger", in comparison to the "primary messenger" action of the monoamines.

In the present method of promoting lean body mass, the forskohlin should be administered in a daily dose of from about 10 to about 60 mg. It is preferred that the daily dose be divided into a plurality of individual doses. It is further preferred that three individual doses be used. In any case, the individual doses are preferably from about 10 to about 20 mg each.

In the present method of treating a mood disorder, the forskohlin should be administered in a daily dose of from about 10 to about 60 mg. It is preferred that the daily dose be divided into a plurality of individual doses. It is further preferred that three individual doses be used. In any case, the individual doses are preferably from about 10 to about 20 mg each.

In either method of the invention, the forskohlin can be administered in combination therapy with additional ingredients. Some examples of additional ingredients are extract from *Garcinia gambogia* in the form of natural (−) hydroxycitric acid or its salts (e.g., calcium or potassium salts); organic salts of vanadium (e.g., bis maltolato vanadium or bis glycinato vanadium); extract from *Piper nigrum* (black pepper) or *Piper longum* (long pepper) containing alkaloid piperine; or extract from *Sida cordifolia* containing alkaloid ephedrine.

The forskohlin can be administered orally, topically or parenterally, although orally is preferred. Carriers, diluents or excipients are well known in the art.

The present invention includes forskohlin compositions. The composition can comprise about 1 to about 40% forskohlin. It is more preferred to include about 5 to about 20% forskohlin. It is even more preferred to include about 8 to about 15% forskohlin. A composition containing about 10% forskohlin is most preferred.

The present invention also includes a method of preparing a forskohlin composition from a forskohlin extract of *Coleus Forskohli* plant, comprising:

(a) providing a forskohlin extract of *Coleus Forskohli* plant;

(b) dissolving the forskohlin extract in a first solvent;

(c) thereafter separating an amount of forskohlin from an amount of impurities in a step comprising combining the product produced in step (b) with a second solvent, wherein the amount of forskohlin is insoluble in the second solvent and the amount of impurities are soluble in the second solvent; and (d) preparing a forskohlin composition by combining the amount of forskohlin obtained in step (c) with at least one physiologically acceptable carrier or excipient to produce a forskohlin composition having a predetermined forskohlin content.

Step (a) of the method includes providing a forskohlin extract of the *Coleus Forskohli* plant. The extract can be obtained in a number of ways, however, the present inventors have devised a preferred method of obtaining the extract.

The content of forskohlin in the plant varies substantially with location, climatic conditions, mode of irrigation and age of the plant. The content usually is between 0.1 to 0.5%. The roots of the plant are washed with water, dried and powdered. A large amount (for example, about 100 kgs) of powdered plant root is subjected to extraction in order to get an appreciable yield of extract.

The roots are subjected to extraction using a suitable solvent. Examples of suitable solvents include toluene, methanol, ethanol, chloroform, ethylacetate, ethylenedichloride, and the like. A mixture of toluene and methanol in a ratio of about 100:1 to about 100:2 is preferred. A ratio of about 100:1 is most preferred.

The volume of solvent mixture and the number of extraction cycles are determined based on the type of extractor used. Normally, about 10 volumes of the solvent mixture are preferred in a continuous-type solvent extractor or Soxhlet extractor.

Ideally, the extraction is performed at a temperature ranging from about 35° to 105° C. The preferred temperature is between about 60° to about 75° C. Extraction time is usually about 6 hours. The efficiency of the extraction is increased when the extraction is performed with pressure, for example, 1 kilo.

After the extraction has been performed a number of times to give an appreciable yield, the extracts are combined, filtered and concentrated under vacuum at low temperatures, preferably at less than 60° C. The use of a thin film evaporator, rotary film evaporator or agitated wiped film evaporator is preferred for concentrating the extract in order to avoid decomposition of the forskohlin, which is temperature sensitive. After the solvent is removed from the system, an extract is obtained in the form of a paste.

Step (b) of the method provides that the forskohlin extract is dissolved in a first solvent. Any of the solvents used in the extraction of the forskohlin can be used at this stage, e.g. toluene, methanol, ethanol, chloroform, ethylacetate, ethylenedichloride, and the like. Toluene is preferred. The paste is dissolved in a minimum amount of the first solvent.

Step (c) of the method includes separating an amount of forskohlin from an amount of impurities. This separating step includes combining the dissolved extract/first solvent produced in step (b) with a second solvent. The forskohlin is insoluble in the second solvent and the impurities are soluble in the second solvent. Thus, the impurities remain in solution, while the forskohlin separates out of the second solvent.

Any solvent in which forskohlin is insoluble can be used as the second solvent. It is preferred, however, that a solvent is chosen in which a large amount of impurities associated with the extract are soluble, so that the resultant forskohlin obtained in this step is substantially more pure than it was in extract form. Petroleum ether (having a boiling point in the range of 60° to 80° C.) is most preferred.

The second solvent is preferably combined with the dissolved extract/first solvent produced in step (b) at a ratio of first solvent to second solvent ranging from about 1:10 to about 1:20. A ratio of about 1:20 is more preferred. Preferably, the resultant mixture is agitated at a temperature ranging from 40° to 60° C. for a few hours, preferably about 2 hours. Forskohlin is insoluble at this temperature and at this solvent ratio.

The forskohlin is thereafter collected (for example, via filtration) and preferably again dissolved in a minimum quantity of first solvent. The second solvent is thereafter added, this time preferably in a ratio of first solvent to second solvent of about 1:25. The resultant mixture is thereafter preferably again agitated at a temperature ranging from 40° to 60° C. for a few hours, preferably about 2 hours. The insoluble product is again collected, and the process may be repeated several times in order to obtain forskohlin of the required purity.

Normally, the purification process described above is performed three times to obtain a product containing about 15 to about 20% forskohlin, which is usually sufficient for most purposes, although higher purities are certainly well within the skill of an ordinary worker. The product preferably contains from about 15 to about 40% forskohlin, although the process of the invention is unique in that it can provide 100% pure forskohlin. The remainder of the product is organic material from the *Coleus Forskohli* plant. The yield is usually about 1.5 kgs of product for every 100 kgs of *Coleus Forskohli* root.

The product obtained in step (c) is normally hygroscopic, and not convenient to use as such. Therefore, step (d) of the present method includes preparing a forskohlin composition by combining this product with at least one physiologically acceptable carrier or excipient to produce a forskohlin composition having a predetermined forskohlin content. Preferable excipients are, for example, magnesium oxide, magnesium carbonate, dicalcium phosphate, and the like. The quantity of excipients used is, of course, based on the predetermined forskohlin content. Standardization of about 1 to about 40% forskohlin is normally achieved, however, depending on the specific need, this product can be upgraded to contain up to 100% forskohlin. This is accomplished by a column chromatography technique, followed by re-crystallization. Preferred standardization is to about 5 to about 20% forskohlin, more preferred about 8 to about 15%, most preferably about 10%.

The forskohlin compositions prepared by the above method are stable. The stability of the compositions has been determined by subjecting the compositions to normal ambient storage conditions, as well as to accelerated storage conditions. During this study, the quality has been tested for stability indicating parameters. As per the study, the extract is stable for a period of not less than 5 years, when it is stored under normal ambient storage conditions.

The present invention includes products (i.e., compositions) produced by this method. The products can usually contain about 1 to about 40% forskohlin, although up to 100% pure forskohlin is possible. Preferred amounts are about 5 to about 20% forskohlin, more preferred about 8 to about 15%, most preferably about 10%.

The present invention also includes methods of promoting lean body mass and methods of treating a mood disorder using the compositions produced by the above-referenced method. Similar dosage levels are effective as those used for conventional forskohlin compositions.

The specifications of an example forskohlin composition prepared according to the described method are as follows:

| | |
|---|---|
| Description | brown powder with a characteristic odor |
| Identification | to comply with standard by thin layer chromatography |
| Loss on Drying | not more than 10.0% |
| Solubility in Water | insoluble |
| Solubility in Alcohol | not less than 45.0% |
| Heavy Metals | not more than 20 ppm |
| Arsenic | not more than 1 ppm |
| Lead | not more than 4 ppm |
| Bulk Density | between 0.4 and 0.7 g/mL |
| Sieve Test | not less than 100.0% passes through 20 mesh |
| | not less than 75.0% passes through 40 mesh |
| | not less than 50.0% passes through 80 mesh |
| Content of Forskohlin by HPLC | not less than 10.0% and not more than 11.0% |

Reasonable modifications of the inventions disclosed herein are well within the scope of those skilled in the art, and are also intended to be within the scope of the present invention. The scope of the present invention is not intended to be limited by the specific examples set out herein, but rather is to be interpreted according to the following claims.

We claim:

1. A method of promoting lean body mass in a human individual in need thereof, comprising administering to the individual a lean body mass promoting effective amount of forskohlin.

2. The method of claim 1, wherein the forskohlin is administered in a daily dose of about 10 to about 60 mg.

3. The method of claim 2, wherein the daily dose is divided into a plurality of individual doses.

4. The method of claim 1, wherein the forskohlin is administered in an individual dose of about 10 to about 20 mg.

5. A method of shifting the proportion between lean body mass and adipose tissue in favor of lean body mass in a human individual in need thereof, comprising administering to the individual a proportion shifting effective amount of forskohlin.

6. The method of claim 5, wherein the forskohlin is administered in a daily dose of about 10 to about 60 mg.

7. The method of claim 6, wherein the daily dose is divided into a plurality of individual doses.

8. The method of claim 5, wherein the forskohlin is administered in an individual dose of about 10 to about 20 mg.

* * * * *

UNITED STATES PATENT AND TRADEMARK OFFICE
CERTIFICATE OF CORRECTION

PATENT NO. : 5,804,596 Page 1 of 1
APPLICATION NO. : 08/807652
DATED : September 8, 1998
INVENTOR(S) : Muhammed Majeed et al.

It is certified that error appears in the above-identified patent and that said Letters Patent is hereby corrected as shown below:

Title Page -

Item [75], Inventors, please correct the second inventor's name from "Vladimir Badmaey" to -- Vladimir Badmaev --.

Signed and Sealed this

Fifth Day of September, 2006

JON W. DUDAS
*Director of the United States Patent and Trademark Office* even

(12) EX PARTE REEXAMINATION CERTIFICATE (8236th)
United States Patent
Majeed et al.

(10) Number: US 5,804,596 C1
(45) Certificate Issued: May 17, 2011

(54) METHOD OF PREPARING A FORSKOHLIN COMPOSITION FROM FORSKOHLIN EXTRACT AND USE OF FORSKOHLIN FOR PROMOTING LEAN BODY MASS AND TREATING MOOD DISORDERS

(75) Inventors: Muhammed Majeed, Piscataway, NJ (US); Vladimir Badmaev, Piscataway, NJ (US); R. Rajendran, Bangalora (IN)

(73) Assignee: Sami Labs Ltd., Bangalore (IN)

Reexamination Request:
No. 90/007,327, Dec. 1, 2004

Reexamination Certificate for:
Patent No.: 5,804,596
Issued: Sep. 8, 1998
Appl. No.: 08/807,652
Filed: Feb. 27, 1997

(51) Int. Cl.
*A61K 31/352* (2006.01)
*A61K 36/53* (2006.01)
*A61P 3/04* (2006.01)
*A61P 43/00* (2006.01)

(52) U.S. Cl. ........................................................ 514/455
(58) Field of Classification Search ........................ None
See application file for complete search history.

(56) References Cited

U.S. PATENT DOCUMENTS

| | | | | |
|---|---|---|---|---|
| 4,476,140 A | 10/1984 | Sears et al. | ................... | 424/283 |
| 4,525,359 A | 6/1985 | Greenway, III et al. | ..... | 514/653 |
| 5,679,358 A | 10/1997 | Bombardelli et al. | ....... | 424/401 |

FOREIGN PATENT DOCUMENTS

| | | |
|---|---|---|
| AU | 34061/89 | 9/1989 |
| EP | 0 341 527 | 11/1989 |
| JP | 59-155313 | 9/1984 |
| JP | 6-133731 | 5/1994 |
| JP | 06-133731 | * 5/1994 |
| JP | 8-169896 | 7/1996 |

OTHER PUBLICATIONS

Merriam–Webster's Collegiate Dictionary, tenth edition (1998) pp. 801 and 933.*
Burns et al., *Clin. Res.* 29(5), 870A, 1981 (abstract only).
Greenway et al., *Clin. Ther.* 9(6), 663–669, 1987.
Gokmen–Polar et al., *Am. J. Physiol.* 270(2), C562–C569, 1996.
Karege et al., *Neuropsychobiol.* 26, 129–135, 1992.
Okuda et al., *J. Lipid Res.* 33, 225–231, 1992.
Sano, "Forskolin and adenylate cyclase", 1983 (Japanese–language only).
Burns et al., *Life Sci.* 31, 815–821, 1982.
Ui, "The role of cyclic AMP in lipid metabolism", 1971 (Japanese–language only).
Greenway et al., *Obesity Res.* 3(Suppl), 561S–568S, 1995.
Schimmel, *Am. J. Physiol.* 246, C63–C68, 1984.

* cited by examiner

*Primary Examiner*—Evelyn Huang

(57) ABSTRACT

A method of promoting lean body mass in an individual is disclosed, comprising administering to the individual a lean body mass promoting effective amount of forskohlin. A method of treating a mood disorder is also disclosed, comprising administering to a patient in need thereof a mood disorder treating effective amount of forskohlin. Compositions suitable for promoting lean body mass and/or treating a mood disorder are also disclosed, the composition comprising about 1 to about 40% forskohlin in combination with at least one physiologically acceptable carrier or excipient. A method of preparing a forskohlin composition from a forskohlin extract of Coleus Forskoli plant is further disclosed, as well as a forskohlin composition prepared by the method.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-8 are cancelled.

* * * * *